(12) United States Patent
Georgopoulos et al.

(10) Patent No.: US 11,077,088 B2
(45) Date of Patent: Aug. 3, 2021

(54) COMPOSITION AND APPARATUS FOR TREATMENT OF CHEMOTHERAPY INDUCED ALOPECIA

(71) Applicant: Paxman Coolers Ltd, Huddersfield (GB)

(72) Inventors: Nikolaos Georgopoulos, Huddersfield (GB); Andrew Collett, Huddersfield (GB); Richard Paxman, Huddersfield (GB)

(73) Assignee: Paxman Coolers Ltd, Huddersfield (GB)

( * ) Notice: Subject to any disclaimer, the term of this patent is extended or adjusted under 35 U.S.C. 154(b) by 0 days.

(21) Appl. No.: 16/312,642

(22) PCT Filed: Jun. 20, 2017

(86) PCT No.: PCT/GB2017/051804
§ 371 (c)(1),
(2) Date: Dec. 21, 2018

(87) PCT Pub. No.: WO2017/220998
PCT Pub. Date: Dec. 28, 2017

(65) Prior Publication Data
US 2019/0240192 A1     Aug. 8, 2019

(30) Foreign Application Priority Data

Jun. 22, 2016 (GB) .................................... 1610910

(51) Int. Cl.
| | | |
|---|---|---|
| *A61K 31/352* | (2006.01) | |
| *A61F 7/10* | (2006.01) | |
| *A61K 31/198* | (2006.01) | |
| *A61P 17/14* | (2006.01) | |
| *A61K 9/00* | (2006.01) | |
| *A61K 31/375* | (2006.01) | |
| *A61F 7/02* | (2006.01) | |
| *A61F 7/00* | (2006.01) | |

(52) U.S. Cl.
CPC .............. *A61K 31/352* (2013.01); *A61F 7/10* (2013.01); *A61K 9/0014* (2013.01); *A61K 31/198* (2013.01); *A61K 31/375* (2013.01); *A61P 17/14* (2018.01); *A61F 2007/0008* (2013.01); *A61F 2007/0287* (2013.01)

(58) Field of Classification Search
CPC ...... A61F 2007/0008; A61F 2007/0287; A61F 7/10; A61K 31/198; A61K 31/352; A61K 31/375; A61K 9/0014; A61P 17/14
See application file for complete search history.

(56) References Cited

U.S. PATENT DOCUMENTS

| | | | | |
|---|---|---|---|---|
| 4,425,916 A | * | 1/1984 | Bowen .................... | A61F 7/106 607/110 |
| 6,150,405 A | * | 11/2000 | Proctor .................... | A61K 8/46 514/474 |
| 2002/0034484 A1 | * | 3/2002 | Lacharriere ............. | A61P 17/14 424/70.1 |
| 2004/0180102 A1 | * | 9/2004 | Patt ........................ | A61K 38/04 424/729 |
| 2005/0191370 A1 | * | 9/2005 | De La Charriere ... | A61K 8/676 424/641 |
| 2008/0069779 A1 | * | 3/2008 | Tamarkin ............... | A61K 9/124 424/45 |

* cited by examiner

*Primary Examiner* — Umamaheswari Ramachandran
(74) *Attorney, Agent, or Firm* — Head, Johnson, Kachigian & Wilkinson, PC

(57) ABSTRACT

A composition for use in cooling therapy and treatment of chemically induced alopecia (CIA), said composition containing a reactive oxygen species (ROS) inhibitor.

2 Claims, 8 Drawing Sheets

COMPOSITION AND APPARATUS FOR TREATMENT OF CHEMOTHERAPY INDUCED ALOPECIA

The invention to which this application relates is a composition and the use of that composition with an apparatus to combat chemotherapy induced alopecia (CIA), chemotherapy drug-induced hair loss, hair follicle death and/or anagen effluvium.

Although the following description refers exclusively to prevention of chemotherapy drug-induced toxicity in human keratinocytes and in particular scalp hair follicles, the person skilled in the art will appreciate that the present invention could be employed with hair follicles on different parts of the body or indeed on different animals.

Chemotherapeutic agents induce CIA by interfering with the transition between the stages of the hair follicle development, stimulating follicular dystrophy or the induction of premature follicle regression {Paus et al. 1994; Trueb, 2009; Yeager et al. 2011}. Telogen effluvium occurs when a larger proportion of hairs in anagen progress prematurely into the telogen phase; for example, cyclophosphamide causes CIA by this mechanism {Patel et al. 2014}. Anagen effluvium, is the most common kind of CIA, because at any given time up to 90% of scalp hair is in anagen and occurs within days to a few weeks after the administration of cytotoxic agents {Olsen et al. 2011}; it is stimulated by alkylating agents, antimetabolites, vinca alkaloids, topoisomerase inhibitors, anthracyclines and taxanes {Espinosa et al. 2003; Yun et al. 2007}. The hair follicle is particularly sensitive to chemotherapy drugs because, as mentioned above, up to 90% of them are in anagen {Batchelor et al. 2001} with their associated matrix keratinocytes representing the most rapidly dividing cell subset, thus they are especially targeted by cell replication-targeting agents.

Currently, scalp cooling represents the only available approach to prevent chemotherapy induced alopecia and may interfere with CIA via a variety of possible mechanisms. Firstly cooling causes blood vessel vasoconstriction, which has been shown to reduce blood flow in the scalp to 20-40% of the normal rate (Janssen et al. 2007). It has been suggested that this will result in less chemotherapeutic drug being delivered to the hair follicles (Bülow et al. 1985). Another possibility is that the rate of drug diffusion across a plasma membrane may be reduced by cooling and thus lower effective drug doses may enter the cells (Lane et al. 1987). Moreover, as cell division is metabolism-driven, it is possible that this process could be decelerated by cooling as temperature can particularly affect phases such as G1 and S (Watanabe and Okada. 1967), which could be especially important for drugs that target specific phases of the cell cycle, such as microtubule-destructive drugs targeting mitosis. Also a decrease in the metabolic activity of the cells in the hair follicle could cause a more general reduction in the cytotoxicity of chemotherapy drugs (Bülow et al. 1985). In practice, it is likely that a combination of these methods has a role in the success of scalp cooling in reducing CIA.

In any event scalp cooling does not work in all cases and efficacy varies from person to person.

It is an aim of the present invention to provide a composition for treating chemotherapy drug-induced hair loss, hair follicle death and/or anagen effluvium.

It is a further aim of the present invention to provide an improved method for treating chemotherapy drug-induced hair loss, hair follicle death and/or anagen effluvium.

It is a yet further aim of the present invention to provide a composition combined with an apparatus to improve treatment of chemotherapy drug-induced hair loss, hair follicle death and/or anagen effluvium.

It is a yet further aim of the present invention to provide an improved method of treating chemotherapy drug-induced hair loss, hair follicle death and/or anagen effluvium using a composition and/or apparatus to cool the affected area.

Figure 1:
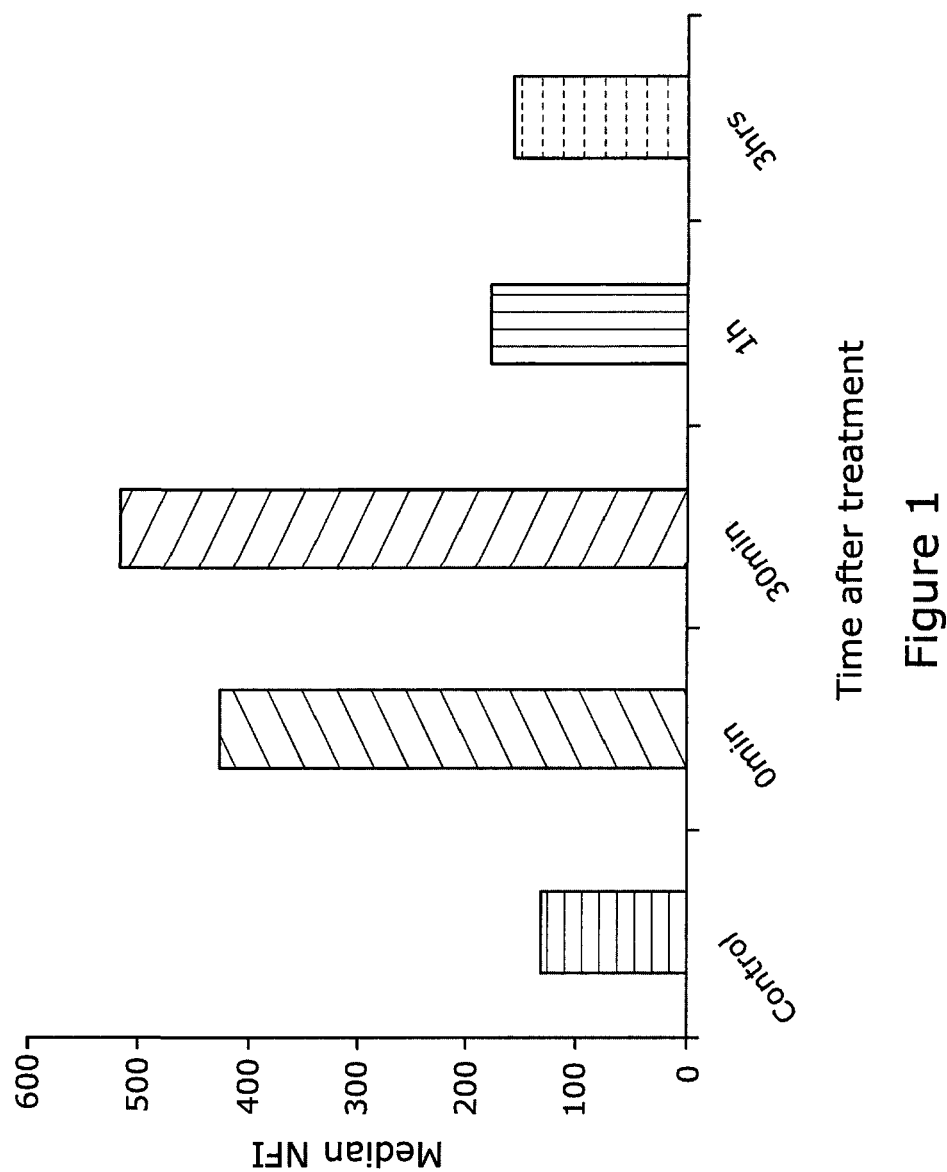
FIG. 1 is a chart showing fluorescence intensity versus time point of fluorescence.

In a first aspect of the invention there is provided a composition containing a reactive oxygen species (ROS) inhibitor for use in cooling therapy for CIA.

Further a method is provided for protecting hair or hair follicles by cooling and by using a composition including a ROS inhibitor. Typically at least the local area of the scalp is cooled to a sub ambient temperature and/or to below body temperature.

Typically the composition includes one or more ROS inhibitors. As such the composition containing one or more ROS inhibitors enhances protection of keratinocytes from chemotherapy drug induced toxicity by combination with cooling therapy, for example in combination with scalp cooling.

In a second aspect of the invention there is a composition comprising a reactive oxygen species (ROS) inhibitor for use in chemotherapy induced alopecia therapy is provided wherein said therapy includes cooling.

In one aspect the invention includes delivery of ROS inhibitory compounds or composition in a controlled temperature environment.

The cooling is typically implemented locally on a body part using a cooling apparatus. Typically the body part is the scalp. Further typically the cooling apparatus is a skull cap and/or the like.

In one embodiment the composition is administered topically. Typically the composition includes a ROS inhibitor that is applied to the body. Further typically the composition containing the ROS inhibitor is applied to the scalp.

In one embodiment the composition is administered in a cooled environment or in a manner in which the surrounding temperature is sub-ambient.

In one embodiment the composition is applied and at least the local temperature reduced and/or cooling is applied.

Typically the temperature is below body temperature (substantially 37° C.). Further typically the composition is applied and the temperature adjacent or surrounding environment is reduced or cooled to 26° C. or below.

In one embodiment the composition is applied and the temperature adjacent or surrounding environment is reduced or cooled to 24° C. or below.

In one embodiment the composition is applied and the temperature adjacent or surrounding environment is reduced or cooled to 22° C. or below. Typically the cooling is to a range substantially at or between 18-26° C.

In a third aspect of the invention there is provided a composition comprising a reactive oxygen species (ROS) inhibitor for use in a method for the treatment of chemotherapy induced alopecia (CIA).

In a further aspect of the invention there is a substance containing a ROS inhibitor for use in a method of scalp cooling as a protector of hair follicles.

Typically the protection is during chemotherapy treatment and/or from CIA.

In one embodiment the substance is provided for topical application. Typically the substance is a fluid such as a cream, gel, paste and/or the like.

In one embodiment the substance is applied to a cooling cap. Typically the substance is applied to a cooling cap before use.

In a further aspect of the invention there is provided use of a compound containing one or more ROS inhibitors, for the manufacture of a medicament for the treatment of CIA by local cooling characterised in that the medicament includes a ROS inhibitor.

This approach combines the use of scalp cooling and inhibitors of the molecular intracellular signalling pathways that mediate the production of ROS in human keratinocytes.

Typically the area or the area of the scalp is cooled using a cooling device (such as the Paxman Orbis cooling cap).

In one embodiment the ROS inhibitor is a cell-permeable antioxidant and/or ROS scavenger. Typically the ROS inhibitor is a direct pharmacological inhibitor.

In one embodiment the ROS inhibitor is N-acetyl-cysteine (NAC).

In one embodiment the ROS inhibitor is synthetic. Typically the inhibitor is synthesised NAC derivative.

In one embodiment the ROS inhibitor includes one or more natural compounds. In one embodiment the ROS inhibitor includes Vitamin C.

In one embodiment the ROS inhibitor includes one or more flavonoids. Typically the ROS inhibitor includes one or more flavanols. In one embodiment the ROS inhibitor includes Quercetin.

In one embodiment the one or more ROS inhibitors are cell-permeable. Typically the ROS inhibitor is a cell-permeable biologic or pharmacological inhibitor that interferes with ROS biosynthesis (ROS generating cell signalling pathways).

In a yet further aspect of the invention there is provided a medicament for the treatment of chemotherapy induced alopecia, said medicament including a ROS inhibitor and a carrier suitable for topical application.

Typically the ROS inhibitor is NAC or a derivative thereof.

Typically the ROS delivery method includes any one or any combination of;
  Topical, by direct absorption by the skin (e.g. via a cream)
  Nanoparticle- or liposome-based targeted route
  Other vector/biological tool (e.g. virus)

In a yet further aspect of the invention there is provided a composition for use in, and/or enhancement of, cooling therapy and treatment of chemically induced alopecia (CIA), said composition containing a reactive oxygen species (ROS) inhibitor.

In a yet further aspect of the invention there is provided an enhancement of cooling therapy treatment of chemically induced alopecia (CIA), using a composition containing a reactive oxygen species (ROS) inhibitor.

EXPERIMENTAL AND EXAMPLES

HaCaTa cells cultured in 6-well plates in KSFM medium and were treated with 3 μg/mL doxorubicin for 2 h at 37° C. and were then labelled with 5 μM of H2DCF-DA (for 30 mins) at the indicated time points post-treatment, to measure levels of intracellular ROS. Cells were then harvested and analysed by flow cytometry. Fluorescence intensity as an indication of intracellular ROS production levels was detected in the FL-1 (or FL-2 channel) and expressed as Median Fluorescence Intensity or MFI (y axis) versus the time point of fluorescence measurement (x axis) in FIG. 1.

The results indicate that the optimal time point for detection of ROS following treatment of cells with a chemotherapeutic drug is 30 mins. At this specific, optimal time point, flow cytometric methodologies permit accurate and sensitive detection of intracellular ROS.

Figure 2:
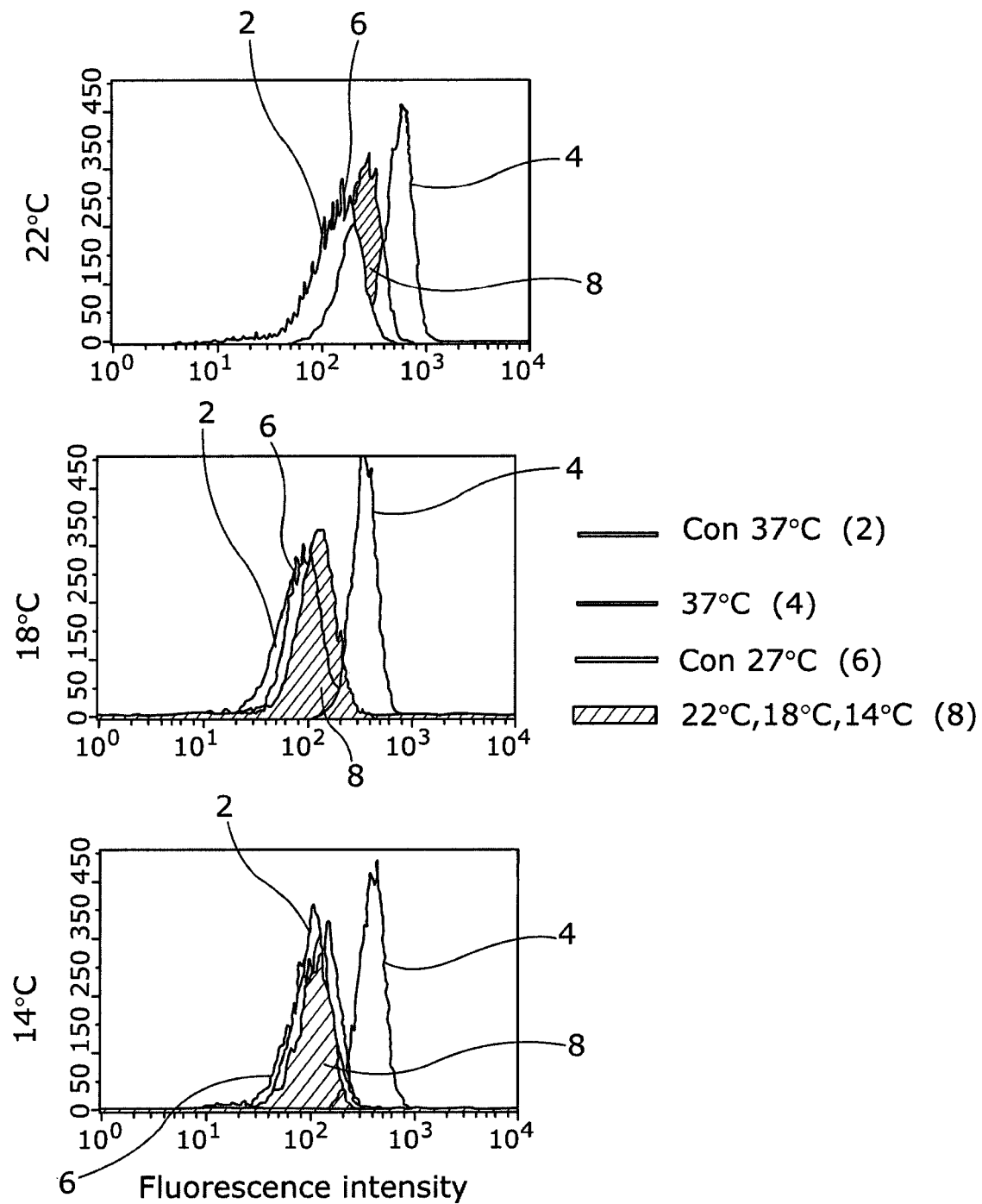
FIG. 2 is a chart showing fluorescence intensity at various temperatures.

Referring to FIG. 2, HaCaTa cells were treated with 3 μg/mL doxorubicin for 2 h at 37° C. or at 22° C., 18° C. & 14° C. to mimic different cooling conditions. As optimised above (FIG. 1), cells were labelled with 5 μM of H2DCF-DA before being analysed by flow cytometry. Representative results are plotted as overlay histograms and the conditions represented are indicated in the legend (right of figure where Con 37° C. is indicated as 2, 37° C. as 4, Con 22° C. as 6, and 22° C., 18° C. & 14° C. as 8).

The results indicate that cooling can prevent the production of ROS in human keratinocytes and the lower the temperature used the less the extent of ROS production. Interestingly, although 22° C. reduces ROS production significantly, lowering the temperature to 18° C. and 14° C. nearly fully attenuates ROS production—which directly correlates with the ability of these two temperatures values to nearly completely prevent cell cytotoxicity in these cells (our published observations, as reported in Al-Tameemi et al 2014).

Figure 3:
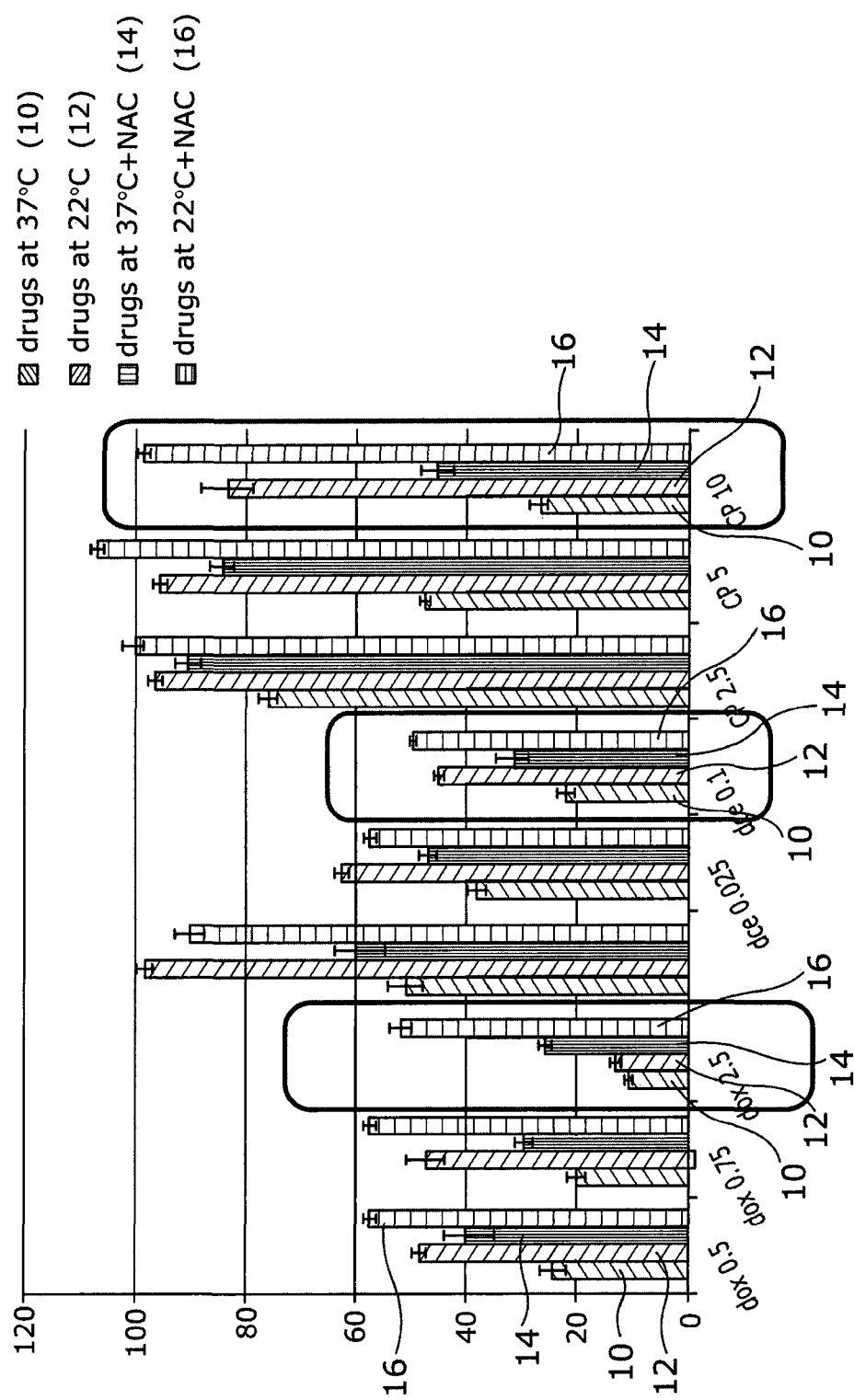
FIG. 3 is a chart showing results of HaCaTa cells treated with a range of drug concentrations with or without NAC.

Referring to FIG. 3, HaCaTa cells were cultured in 96-well plates in KSFM at a density of 5×103/well and cells were incubated overnight at 37° C./5% CO2. Some of the cells were pre-treated with 0.625 mM NAC for 1 h (optimal concentration for NAC was determined by pre-titration experiments). After that, cells were treated with a range of concentrations of docetaxel, doxorubicin (Sigma) or 4-hydroxycyclophosphamide (4-OH-CP), the active metabolite of cyclophosphamide (Niomech), for a period of 2 h at 37° C. (control conditions) or under cooling conditions (22° C.) in the appropriate culture medium with and without NAC (pH 7.4). Solvent (DMSO) controls (representing the maximal amount of DMSO that corresponded to the highest drug concentration) were included in all experiments. Following treatment, drugs were removed, cells washed twice using PBS and fresh culture medium added. Cultures were then incubated at 37° C. for 72 h before cell growth was assessed using CellTiter 96 AQueous One cell proliferation assay (Promega). Briefly, 20 μl of CellTiter reagent was added to each well and the plates were incubated at 37° C. in 5% CO2 conditions for 4 h before Absorbance readings were obtained spectrophotometrically at 492 nm. Results are expressed as relative to control (untreated cells). "dox", "dce" and "CP" denote doxorubicin, docetaxel and 4-OH-CP, respectively. Drug treatment at 37° C. is indicated as 10, drugs at 22° C. as 12, drugs at 37° C.+NAC as 14 and drugs at 22° C.+NAC as 16.

The results indicate that although cooling or treatment with NAC alone can provide some cytoprotection, combination of cooling plus the antioxidant/ROS scavenger NAC provides far better protection than each agent alone. The results were particularly more pronounced for the higher drug concentrations (indicated by the boxes).

Figure 4:
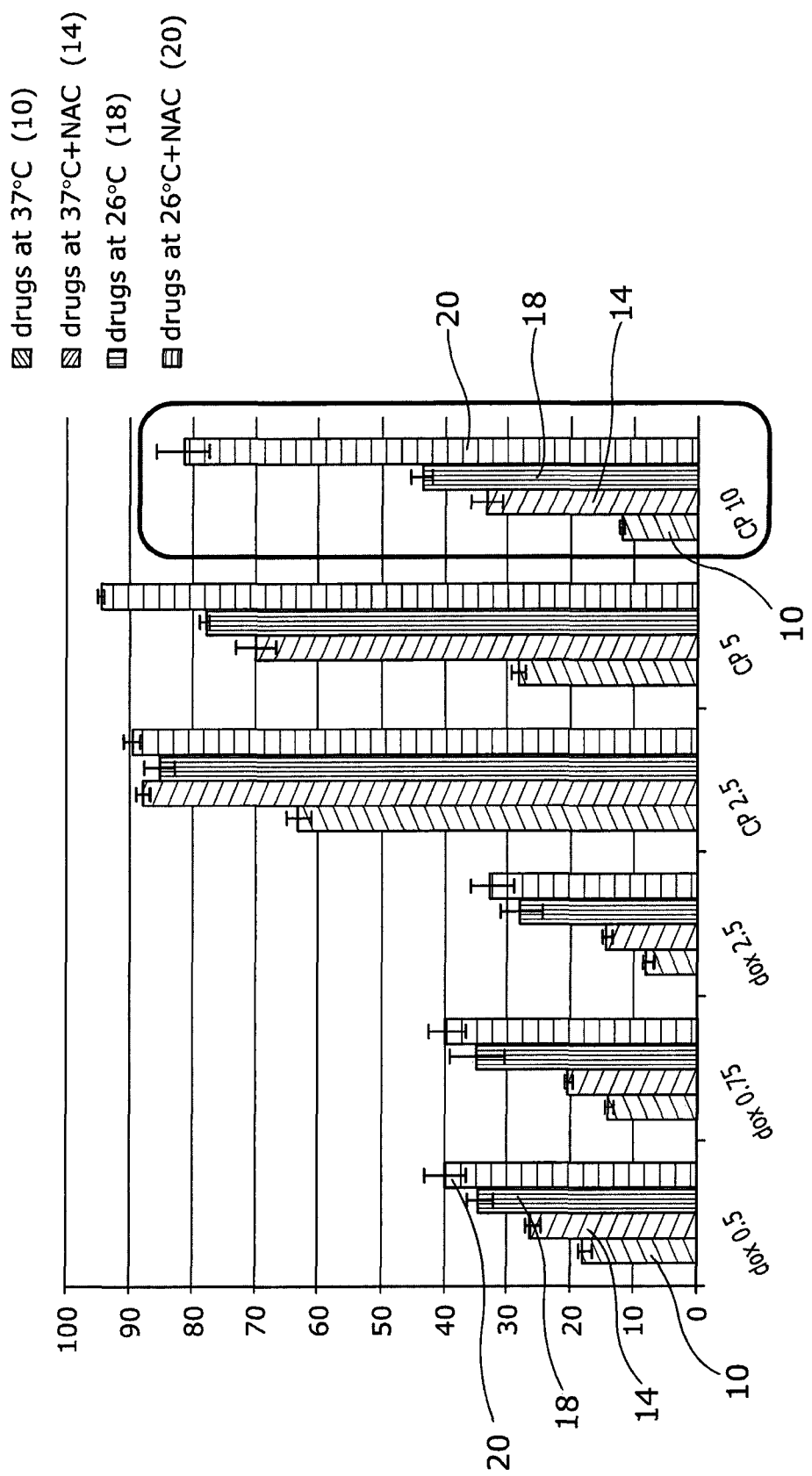
FIG. 4 is a chart showing results of HaCaTa cells treated with a range of drug concentrations.

Referring to FIG. 4, HaCaTa cells were cultured in 96-well plates in KSFM at a density of 5×103/well and cells were incubated overnight at 37° C./5% CO2. Some of the cells were pre-treated with 0.625 mM NAC for 1 h (optimal concentration for NAC was determined by pre-titration experiments). After that, cells were treated with a range of concentrations of doxorubicin (Sigma) or 4-hydroxycyclophosphamide (4-OH-CP, Niomech), for a period of 2 h at 37° C. (control conditions) or under cooling conditions (26° C.) in the appropriate culture medium with and without NAC (pH 7.4). Solvent (DMSO) controls (representing the maximal amount of DMSO that corresponded to the highest drug concentration) were included in all experiments. Following treatment, drugs were removed, cells washed twice using PBS and fresh culture medium added. Cultures were then incubated at 37° C. for 72 h before cell growth was assessed using CellTiter 96 AQueous One cell proliferation assay (Promega). Briefly, 20 μl of CellTiter reagent was added to each well and the plates were incubated at 37° C. in 5% CO2 conditions for 4 h before Absorbance readings were obtained spectrophotometrically at 492 nm. Results are expressed as % relative to control (untreated cells). "dox" and "CP" denote doxorubicin and 4-OH-CP, respectively. Drug treatment at 37° C. is indicated as 10, drugs at 37° C.+NAC as 14, drugs at 26° C. as 18 and drugs at 26° C.+NAC as 20.

The results indicate that although cooling or treatment with NAC alone can provide some cytoprotection, combination of cooling plus the antioxidant/ROS scavenger NAC provides far better protection than each agent alone. The results were particularly more pronounced for the higher drug concentrations (indicated by the boxes). Importantly, when the data in the box in this figure is compared with that in FIG. 3 for the same CP concentration, it is clear that although at 26° C. the cells demonstrate higher levels of cytotoxicity in comparison to 22° C., inhibition of ROS renders cooling at 26° C. highly cytoprotective.

Figure 5:
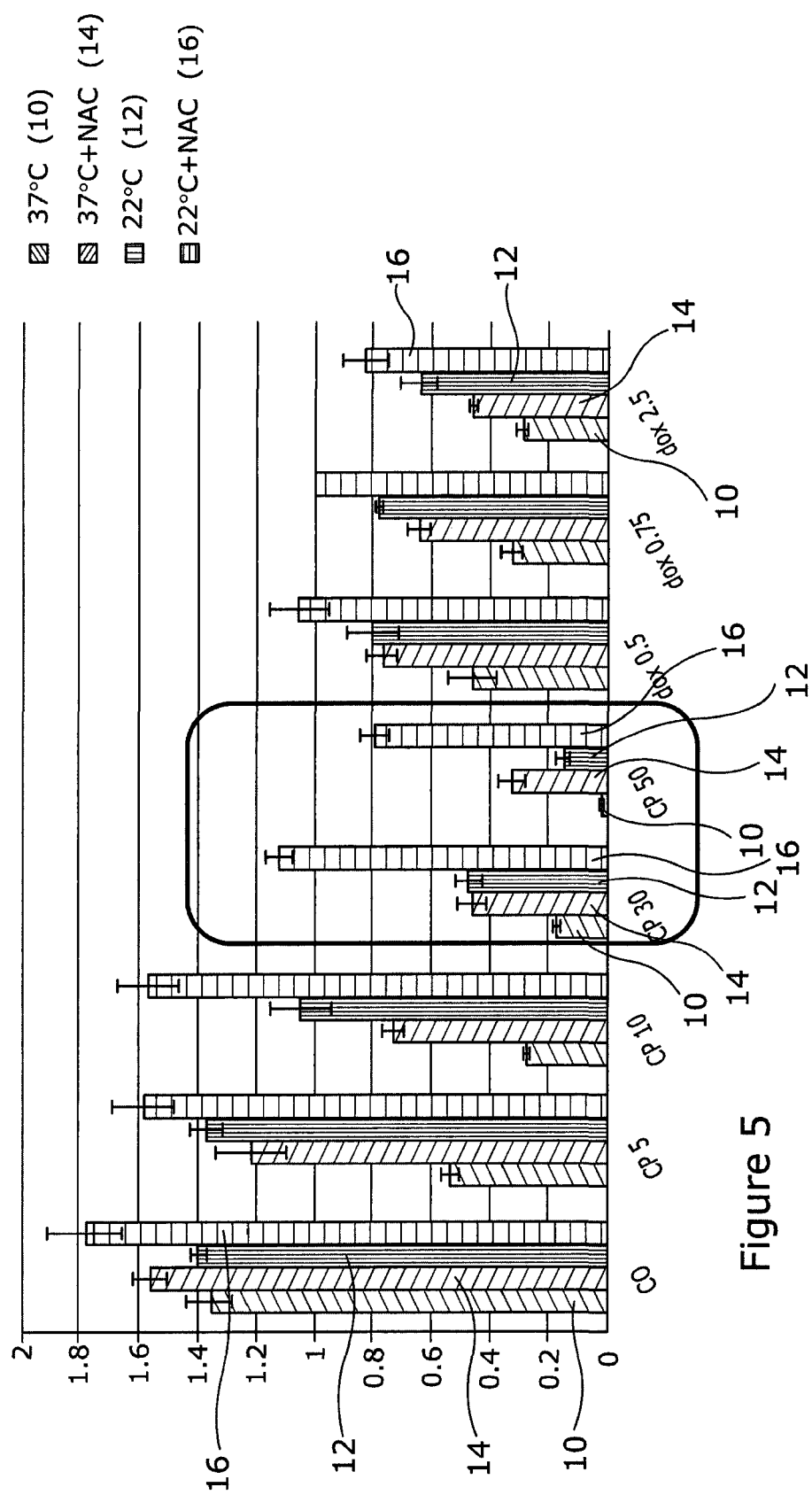
FIG. 5 is a chart showing results of HaCaTa cells treated with a range of drug concentrations.

Referring to FIG. 5, HaCaTa cells were cultured in 96-well plates in KSFM at a density of 5×103/well and cells were incubated overnight at 37° C./5% CO2. Some of the cells were pre-treated with 0.625 mM NAC for 1 h (optimal concentration for NAC was determined by pre-titration experiments). After that, cells were treated with a range of concentrations of doxorubicin (Sigma) or 4-hydroxycyclophosphamide (4-OH-CP, Niomech), for a period of 2 h at 37° C. (control conditions) or under cooling conditions (22° C.) in the appropriate culture medium with and without NAC (pH 7.4). Solvent (DMSO) controls (representing the maximal amount of DMSO that corresponded to the highest drug concentration) were included in all experiments. Following treatment, drugs were removed, cells washed twice using PBS and fresh culture medium added. Cultures were then incubated at 37° C. for 72 h before cell growth was assessed using CellTiter 96 AQueous One cell proliferation assay (Promega). Briefly, 20 μl of CellTiter reagent was added to each well and the plates were incubated at 37° C. in 5% CO2 conditions for 4 h before Absorbance readings were obtained spectrophotometrically at 492 nm. Results are shown as arbitrary Absorbance units. Drug treatment at 37° C. is indicated as 10, drugs at 37° C.+NAC as 14, drugs at 22° C. as 12, and drugs at 22° C.+NAC as 16

The results in this figure enhanced our findings presented in FIG. 3 by expanding the drug concentration range for 4-OH-CP. The results demonstrate that even at extremely high doses of this particular drug (red box) where the dose of the drug results in total cytotoxicity (complete death), the combination of cooling plus ROS inhibitor provides strikingly high levels of protection from drug-induced toxicity.

Figure 6:
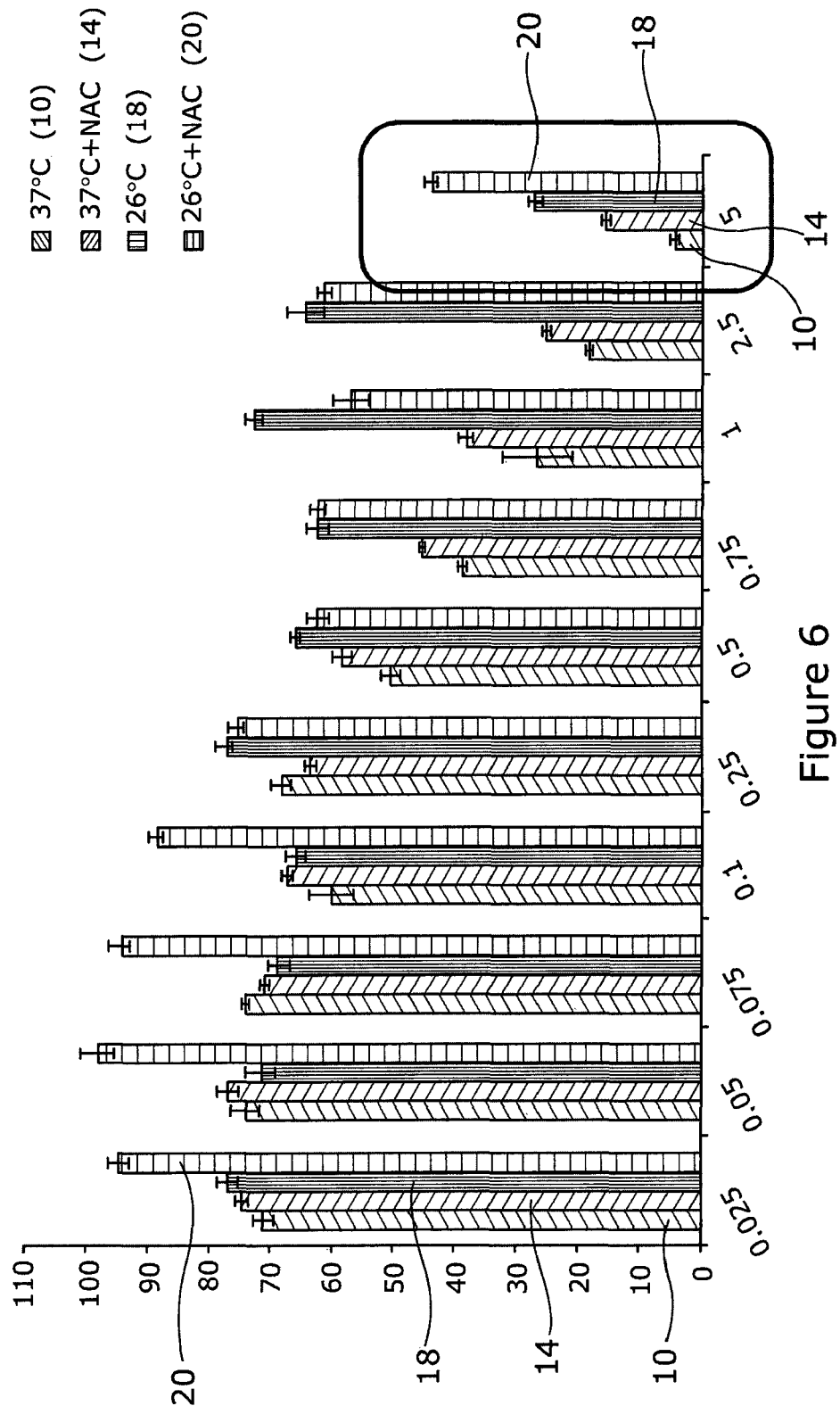
FIG. 6 is a chart showing results of HaCaTa cells treated with a range of drug concentrations.

Referring to FIG. 6, HaCaTa cells were cultured in 96-well plates in KSFM at a density of 5×103/well and cells were incubated overnight at 37° C./5% CO2. Some of the cells were pre-treated with 0.625 mM NAC for 1 h (optimal concentration for NAC was determined by pre-titration experiments). After that, cells were treated with a range of concentrations of doxorubicin (Sigma) for a period of 2 h at 37° C. (control conditions) or under cooling conditions (26° C.) in the appropriate culture medium with and without NAC (pH 7.4). Solvent (DMSO) controls (representing the maximal amount of DMSO that corresponded to the highest drug concentration) were included in all experiments. Following treatment, drugs were removed, cells washed twice using PBS and fresh culture medium added. Cultures were then incubated at 37° C. for 72 h before cell growth was assessed using CellTiter 96 AQueous One cell proliferation assay (Promega). Briefly, 20 μl of CellTiter reagent was added to each well and the plates were incubated at 37° C. in 5% CO2 conditions for 4 h before Absorbance readings were obtained spectrophotometrically at 492 nm. Results are expressed as % relative to control (untreated cells). Drug treatment at 37° C. is indicated as 10, drugs at 37° C.+NAC as 14, drugs at 26° C. as 18 and drugs at 26° C.+NAC as 20.

The results in this figure enhanced our findings presented in FIGS. 3 and 4 by expanding the drug concentration range for doxorubicin. The results demonstrate that even at extremely high doses of this particular drug (red box) where the dose of the drug results in nearly total cytotoxicity (death), the combination of cooling plus ROS inhibitor provides strikingly high levels of protection from drug-induced toxicity even at 26° C.

Figure 7:
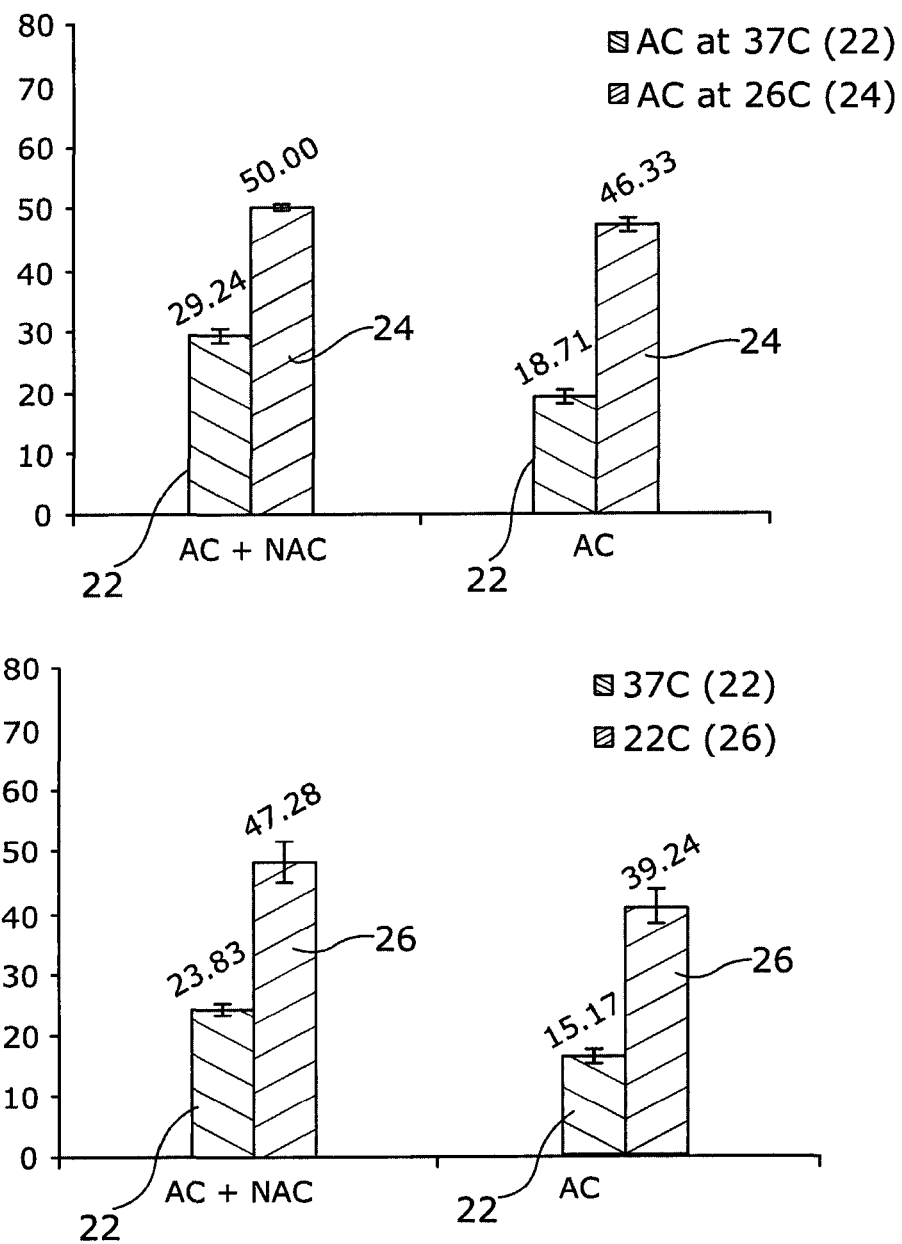
FIG. 7 is a chart showing results of treated HaCaTa cells expressed as a percentage relative to control untreated cells.

Referring to FIG. 7, HaCaTa cells were cultured in 96-well plates in KSFM at a density of 5×103/well and cells were incubated overnight at 37° C./5% CO2. Some of the cells were pre-treated with 0.625 mM NAC for 1 h (optimal concentration for NAC was determined by pre-titration experiments). After that, cells were treated with the combination AC at 37° C. (control conditions) or under cooling conditions (26° C. or 22° C.) in the appropriate culture medium with and without NAC (pH 7.4). In particular, sequential treatment with doxorubicin (A—for Adriamycin) and 4-OH-CP (C, for cyclophosphamide) was carried out using doxorubicin at 3 μg/ml (1 h) and 4-OH-CP at 5 μg/ml (1 h). Cells were then washed and the medium was replaced before cell growth was assessed 72 h later using CellTiter 96 AQueous One cell proliferation assay (Promega). Briefly, 20 μl of CellTiter reagent was added to each well and the plates were incubated at 37° C. in 5% CO2 conditions for 4 h before Absorbance readings were obtained spectrophotometrically at 492 nm. Results are expressed as relative to control (untreated cells). Treatment at 37° C. is indicated as 22, at 26° C. as 24 and at 22° C. indicated as 26.

The results indicate that although cooling at 26° C. or 22° C. demonstrates a significant cytoprotective effect, combination of cooling with the ROS inhibitor/scavenger NAC results in better cytoprotection. These finding demonstrate that cooling plus ROS inhibition protects human keratinocytes better, than does cooling alone, from cytotoxicity caused not only by single but also by combinatorial drug treatment.

Figure 8:
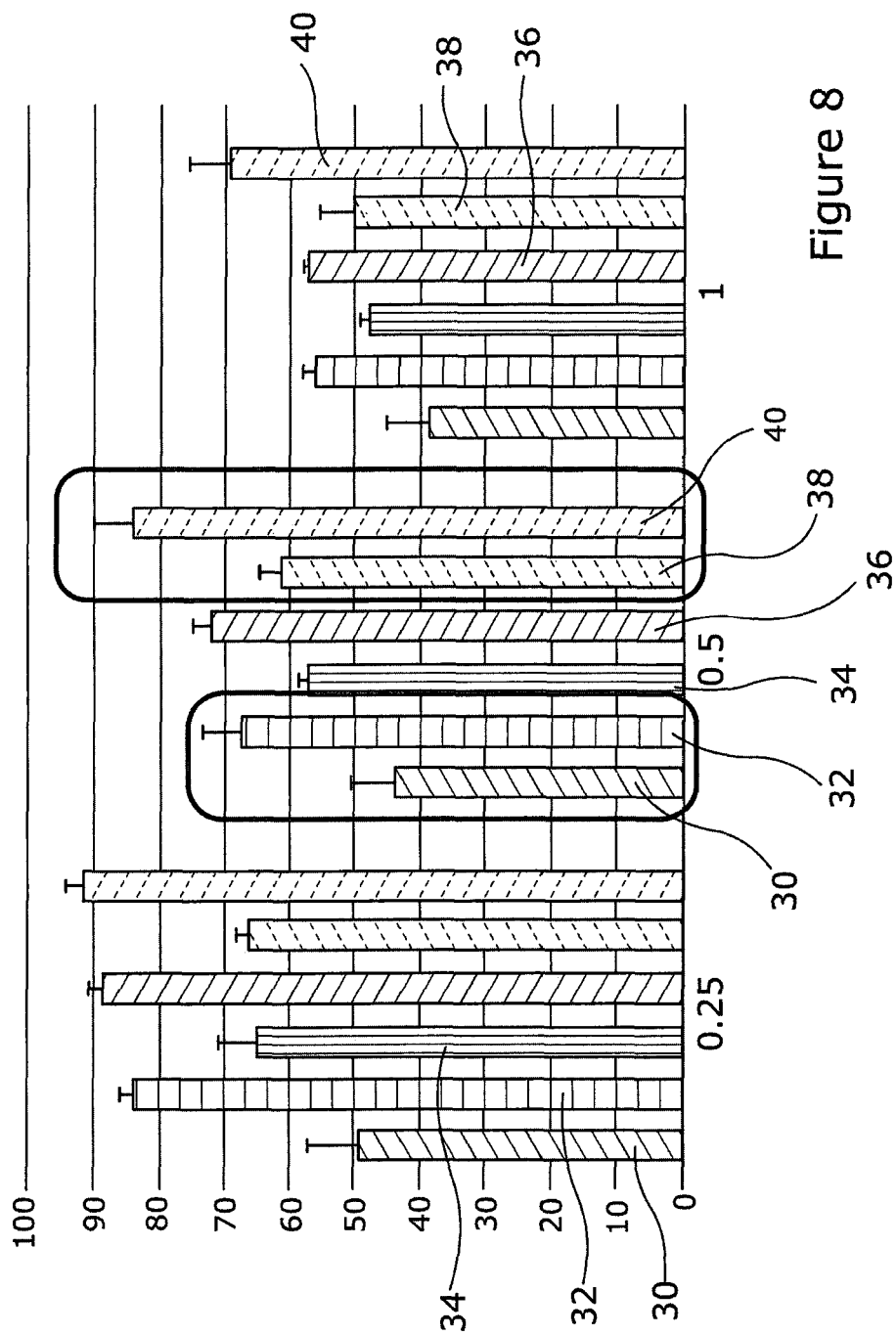
FIG. 8 is a chart showing results of treated HaCaTa cells including use of antioxidant Quercetin.

Results from use of the antioxidant Quercetin is shown in FIG. 8. HaCaTa cells (5×103 cells/well) were cultured in 96-well plates in 100 µl of KSFM per well and incubated overnight at 37° C./5% CO2. After 24 hours the cells were pre-treated with 3 µM Quercetin or 0.625 mM NAC. A control that did not contain any antioxidant was also included. After an hour of pre-treatment, cells were treated with Doxorubicin at 0.25 µg/ml, 0.5 µg/ml and 1 µg/ml. Cells were then incubated for 2 h at 37° C. (control conditions) or under cooling conditions (26° C.). Cultures were then incubated at 37° C. for 72 h before cell growth was assessed using CellTiter 96 AQueous One cell proliferation assay (Promega). Results are expressed as % relative to controls containing antioxidants but without doxorubicin.

The results indicate that although cooling or treatment with Quercetin alone can provide some cytoprotection, combination of cooling plus the antioxidant/ROS scavenger Quercetin provides far better protection than each agent alone (as indicated by the red boxes).

DOX only at 37° C. is indicated as 30, DOX only at 26° C. is indicated as 32, NAC+DOX at 37° C. is indicated as 34, NAC+DOX at 26° C. is indicated as 36, Quercetin+DOX at 37° C. is indicated as 38, and Quercetin+DOX at 26° C. is indicated as 40+NAC as 14, drugs at 26° C. as 18 and drugs at 26° C.+NAC as 20

The invention claimed is:

1. A method for the treatment of chemotherapy induced alopecia to provide protection from drug induced toxicity comprising the steps of: (i) administering topically a composition comprising a reactive oxygen species inhibitor (ROS) to the scalp of a patient (ii) scalp cooling therapy, wherein the ROS inhibitor is selected from N-acetyl-cysteine, Vitamin C, flavonoids, flavonols, quercetin and wherein the ROS inhibitor is cooled after application to temperature of 26° C. or below.

2. A method according to claim 1 wherein the scalp is cooled using a cap.

* * * * *